United States Patent [19]

Lewis et al.

[11] Patent Number: 4,593,114
[45] Date of Patent: Jun. 3, 1986

[54] DIRECT PROCESS FOR PREPARING DIMETHYLSILOXANES

[75] Inventors: Kenrick M. Lewis, New York; Bernard Kanner, West Nyack, both of N.Y.

[73] Assignee: Union Carbide Corporation, Danbury, Conn.

[21] Appl. No.: 739,124

[22] Filed: May 29, 1985

Related U.S. Application Data

[63] Continuation of Ser. No. 650,087, Sep. 13, 1984, abandoned.

[51] Int. Cl.⁴ .............................. C07F 7/08; C07F 7/18
[52] U.S. Cl. .................................... 556/450; 556/452; 556/453; 556/456; 556/457; 556/460
[58] Field of Search ............... 556/450, 452, 453, 456, 556/457, 460

[56] References Cited

U.S. PATENT DOCUMENTS

| | | | |
|---|---|---|---|
| 2,380,995 | 8/1945 | Rochow et al. | 260/607 |
| 2,380,996 | 8/1945 | Rochow et al. | 260/607 |
| 2,380,997 | 8/1945 | Patnode | 252/225 |
| 2,389,931 | 11/1945 | Reed et al. | 260/607 |
| 2,459,539 | 1/1949 | Rochow | 260/448.2 |
| 2,473,260 | 6/1949 | Rochow | 260/448.8 |
| 2,887,502 | 5/1959 | Bluestein | 260/448.2 |
| 3,072,700 | 1/1963 | deWit | 260/448.8 |
| 3,446,829 | 5/1969 | Zock | 260/448.2 |
| 4,044,038 | 8/1977 | Rossnay | 556/452 |
| 4,088,669 | 5/1978 | Malek et al. | 260/448.8 |
| 4,276,425 | 6/1981 | Burkhardt et al. | 556/460 |
| 4,314,908 | 2/1982 | Downing et al. | 252/182 |
| 4,366,324 | 12/1982 | Habata et al. | 556/460 |

FOREIGN PATENT DOCUMENTS

| | | | |
|---|---|---|---|
| 26-286 | 1/1951 | Japan | 556/450 |
| 642997 | 9/1950 | United Kingdom | 556/450 |

OTHER PUBLICATIONS

W. Noll, "Chemistry and Technology of Silicones", Academic Press, NY (1968).
A. Petrov et al., "Synthesis of Organosilicon Monomers", Consultants Bureau, NY (1976).
R. J. H. Voorhoeve, "Organohalosilanes: Precursors to Silicones", Elsevier, NY (1967).
W. Buechner, "Organometallic Chemistry Reviews", Library 9, pp. 409–431, Elsevier Scientific Pub. Co., NY (1980).
Rochow et al., "The Reaction of Ethers wtih Silicon", PB 157357, NTIS, U.S. Dept. of Commerce.
Rochow and Newton, "Organic Derivatives of Silicon", Inorg. Chem. 9, 1071 (1970).
Fredin et al., "Silicon Atom Reactions with Methanol and Di–Methyl–Ether", Abstracts 184th National ACS Meeting, Kansas City, MO, Sep. 12–17, 1982, INOR. #60.
Turetskaya et al., "New Data on the Compositions of Intermediate Compounds in the Direct Synthesis of Chloroorganosilanes", Russ. J. Gen. Chem. 44 (12), 2738 (1975).
Speier et al., Abstracts 13th Organosilicon Symposium, Univ. of Michigan, Mar. 30–31, 1979.
Ward and Carroll, J. Electrochem. Soc. Solid State Sci. Tech. 129 (1), 227 (1982).
Voorhoeve et al., J. Catalysis 4, 123 (1965).
Lobusevich et al., Russ. J. Appl. Chem. 49 (10), 2236 (1976).
D. Kunii et al., Fluidization Engineering, John Wiley & Sons, NY (1969).
Zubkov et al., Dokl. Akad. Nauk, SSR 159 (3), 599 (1964); 188 (3), 594 (1969).
Miyamura et al., Surf. Sci. 72, 243 (1978).
Lobusevich, et al., Russ. J. Appl. Chem. 49(10), 2158 (1976).

Primary Examiner—Paul F. Shaver
Attorney, Agent, or Firm—Paul W. Leuzzi

[57] ABSTRACT

A process is disclosed for the direct synthesis of cyclic and oligomeric organosiloxanes, such as dimethylsiloxanes, comprising reacting a hydrocarbon ether and a hydrocarbon halide with a fluidized or agitated bed of activated silicon particles with a maximum contact time of five minutes, and continuously withdrawing products from that reaction.

36 Claims, No Drawings

DIRECT PROCESS FOR PREPARING DIMETHYLSILOXANES

This application is a continuation of prior U.S. application Ser. No. 650,087 9/13/84, now abandoned.

BACKGROUND OF THE INVENTION

1. Field of the Invention

The present invention relates to a process for preparing siloxanes; more particularly and in a preferred embodiment, the present invention is a direct process for the preparation of cyclic and oligomeric dimethylsiloxanes by the fluidized bed reaction of copper-activated silicon with dimethyl ether and a methyl halide.

2. Description of the Prior Art

Alkylsiloxanes, especially the dimethylsiloxanes, find extensive use in emulsions, antifoams and pastes on account of their low surface tension, high surface activity, good spreading power, chemical inertness and thermal stability.

The direct synthesis of the dimethylsiloxanes from dimethyl ether and suitably activated silicon has been of interest for many years. This has been so because a successful synthesis would reduce the cost and complexity associated with the state-of-the-art process. Currently, a mixture of methylchlorosilanes is made by the Rochow Direct Reaction (see, e.g., U.S. Pat. No. 2,380,995). This mixture is separated via a multiplate distillation to obtain high purity dimethyldichlorosilane, which is subsequently hydrolyzed to cyclic and linear dimethylsiloxanes and HCl (equation 1):

$$n(CH_3)_2SiCl_2 + nH_2O \rightarrow [(CH_3)_2SiO]_n + 2n\ HCl \quad (1)$$

n=3, 4, 5, 6, 7, 8.

Descriptions of the state-of-the-art technology are given in the monographs

W. Noll, "Chemistry and Technology of Silicones", Academic Press, N.Y. (1968);

A. Petrov et. al., "Synthesis of Organosilicon Monomers", Consultants Bureau, N.Y. (1976); and R. J. H. Voorhoeve, "Methylchlorosilanes: Precursors to Silicones", Elsevier, N.Y. (1967);

and in the review

W. Buechner, "Organometallic Chemistry Reviews", Library 9, pp 409–431.

Corrosion and pollution problems attend the handling and recovery of the liberated HCl. However, the gas may be recycled to the synthesis of $HSiCl_3$ or used to prepare $CH_3Cl$ from $CH_3OH$ for the Rochow Direct Reaction. Some silicones manufacturers use methanol in place of water and obtain $CH_3Cl$ as the by-product (equation 2):

$$n(CH_3)_2SiCl_2 + 2nCH_3OH \rightarrow [(CH_3)_2SiO]_n + 2nCH_3Cl + nH_2O \quad (2)$$

Small amounts of HCl and $(CH_3)_2O$ are also formed, and if not removed, have undesirable effects on the rate and selectivity of the Rochow Direct Reaction (i.e., on the synthesis of the methylchlorosilanes). It is to obviate these complexities that there has been much interest in obtaining the direct synthesis of dimethylsiloxanes from silicon and dimethyl ether (equation 3):

$$n(CH_3)_2O + nSi \rightarrow [(CH_3)_2SiO)]_n \quad (3)$$

Although not wishing to be bound by theory, the overall process proposed by equation (3) may actually involve the intermediate synthesis of dimethyldimethoxysilane followed by hydrolysis to the cyclic and oligomeric dimethylsiloxanes (equation 4):

$$2(CH_3)_2O + Si \xrightarrow{} (CH_3)_2Si(OCH_3)_2 \xrightarrow{H_2O} \quad (4)$$

$$[(CH_3)_2SiO]_n + 2CH_3OH$$

Methanol can be dehydrated to dimethyl ether (equation 5), which could then be recycled.

$$2CH_3OH \rightarrow (CH_3)_2O + H_2O \quad (5)$$

Japanese patent No. 286 (1951) [Chem. Abstr. 47, 3334 (1953)] discloses that dimethyldimethoxysilane and methyltrimethoxysilane were obtained in good yield from the reaction of silicon, containing 10% copper catalyst, and dimethyl ether at 400°–430° C. in a fixed-bed reactor at atmospheric pressure. However, an exhaustive investigation of the reactivity of activated silicon with ethers in fixed-bed reactors by Rochow and Zuckerman ["The Reaction of Ethers with Silicon", PB 157357, NTIS. U.S. Dept. of Commerce] later showed that disclosure to be erroneous (see, e.g., U.S. Pat. No. 4,088,669 at column 1, lines 52–61). Rochow and Newton [Inorg. Chem. 9, 1072 (1970)) also failed to realize methylmethoxysilane formation when the reaction was attempted in a slurry of silicone oil at 300° C. Fredin, et. al., [Abstracts 184th National ACS Meeting, Kansas City, Mo., Mar. 12–17, 1982. #INOR 60] showed that whereas groundstate silicon atoms reacted spontaneously with methanol at 10° K. in an argon matrix, no reaction was observed with dimethyl ether. Photoexcitation of the Si atoms was necessary in order to achieve insertion into the C—O bond of the dimethyl ether.

The co-reaction of mixtures of dimethyl ether and hydrogen chloride with silicon-copper mixtures and contact masses has been disclosed by Rochow (U.S. Pat. No. 2,459,539), by Burgess [British Patent No. 642,997) and by Turetskaya, et. al. (Russ. J. Gen. Chem. 44(12), 2738 (1975)). In each case the principal products were methylchlorosilanes. Presumably, methylchloride was first formed (equation 6) and it then reacted with silicon to give the methylchlorosilanes.

$$(CH_3)_2O + 2HCl \rightarrow 2CH_3Cl + H_2O \quad (6)$$

U.S. Pat. No. 4,088,669 discloses that dimethyldimethoxysilane is the main product from the reaction of dimethyl ether and methylbromide with activated silicon at 200°–300° C. under autogenous conditions. The patent specifies that a closed reaction vessel is necessary in order to get dimethyl ether to react with silicon and that activating traces of tin, mercury and copper and long reaction times (1–100 hr) were essential to the success of the synthesis. More particularly, Example 13 of the patent indicates that no reaction product was obtained, under a variety of reaction conditions, when gaseous dimethyl ether was continuously passed through a fixed bed of powdered, copper-activated silicon. The overall process was thought to proceed as described in equations 7–9 [Speier, et. al., Abstracts 13th Organosilicon Symposium, Univ. of Michigan, Mar. 30–31, 1979; see also, column 4, lines 16–22, of U.S. Pat.

No. 4,088,669]. The patent describes CH$_3$Br as having a catalytic function.

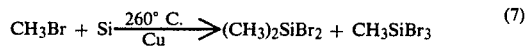
$$CH_3Br + Si \xrightarrow[Cu]{260° C.} (CH_3)_2SiBr_2 + CH_3SiBr_3 \quad (7)$$

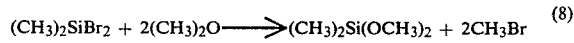
$$(CH_3)_2SiBr_2 + 2(CH_3)_2O \longrightarrow (CH_3)_2Si(OCH_3)_2 + 2CH_3Br \quad (8)$$

$$CH_3SiBr_3 + 3(CH_3)_2O \longrightarrow CH_3Si(OCH_3)_3 + 3CH_3Br \quad (9)$$

The method disclosed in said U.S. Pat. No. 4,088,669 is attended by serious disadvantages when applied on a large scale. The confinement of a large mass of reacting silicon particles in a closed vessel and maintenance of said mass at a uniform temperature between the limits (200°–300° C.) specified therein necessitate special means to obtain adequate heat-transfer and mass transfer through the reaction mixture in order to avoid hot-spots. Hot-spots lead to pyrolysis of the methyl bromide and dimethyl ether and the formation of surface deposits which inhibit further reaction of the silicon mass. Both dimethyl ether (critical temperature 129° C.) and methyl bromide (critical temperature 194° C.) have critical temperatures less than the lower temperature limit set forth in the patent. Consequently, they are both gaseous under the reaction conditions specified. Agitation (e.g., by stirring, rocking or shaking) of the mass is required in order to obtain adequate heat transfer and continually expose fresh surface for reaction. Problems associated with stirring large masses of abrasive silicon particles have been discussed in U.S. Pat. Nos. 2,887,502 and 2,389,931 and are well known to those skilled in the art of the Rochow synthesis. While the use of an inert solvent, as specified in U.S. Pat. No. 4,088,669, reduces the heat and mass transfer problems, said solvent must be free of impurities which inhibit the synthesis of dimethyldimethoxysilane. Recycle of the solvent is essential for the economic practice of this synthesis. Hence additional processing steps (e.g., filtration and distillation) which add to the complexity of the synthesis are required.

Contrary to these teachings, it has now surprisingly been found that the direct synthesis of organosiloxanes and their precursors may be accomplished successfully in a fluidized or agitated bed reactor with contact times substantially less than one hour.

SUMMARY OF THE INVENTION

The present invention is a process for the direct synthesis of cyclic and oligomeric organosiloxanes comprising reacting a hydrocarbon ether and a hydrocarbon halide with a fluidized or agitated bed of activated silicon particles with a maximum contact time of five minutes and continuously withdrawing products from that reaction.

DESCRIPTION OF THE PREFERRED EMBODIMENTS

In its preferred form, the direct synthesis of this invention is performed in a conventional gas-solid reactor such as a stirred-bed or fluidized-bed reactor. It is necessary that the reactor system not be closed. That is, arrangements must be made for the continuous withdrawal or removal of the products of the direct synthesis. This may be accomplished using conventional techniques and equipment. Accordingly, the reaction temperature must be greater than the boiling points of the reactants and products. The boiling points referred to here are not necessarily those at 760 mm Hg, but those appropriate to the pressure conditions in the reactor. A conventional means of cooling and condensing the hot product mixture in a vessel separate from but directly attached to the gas-solid reactor may also be provided if desired.

It is also necessary that the activated silicon particles be maintained in a state of agitation (i.e., stirred or fluidized) so as to facilitate heat- and mass-transfer and avoid hot spots in the reaction medium. Other operational details pertinent to gas-solid reactors are well known to those skilled in the art and thus will not be fully described herein. The same reactor may be used for silicon activation and subsequent reaction with hydrocarbon halide and hydrocarbon ether. Alternatively, the silicon activation and reaction may be conducted in separate reactors, provided the activated silicon is transported to the second reactor in an inert atmosphere.

Pure silicon does not react with the hydrocarbon halide, methyl chloride, below about 400° C. As pointed out above, even atomic silicon is unreactive towards the hydrocarbon ether, dimethyl ether. Hence the silicon must be activated in order that the combined reaction with the hydrocarbon ether and hydrocarbon halide can be successful. The preferred activator is copper because it allows the lowest reaction temperatures to be used. Silver is also suitable. It is essential that the activator (e.g., copper) and silicon be in intimate contact to permit diffusion of copper or other activator into the silicon and the formation of an alloy or solid-solution. Copper has a high diffusion rate in silicon and this rate increases with temperature [Ward and Carroll, *J. Electrochem. Soc. Solid State Sci. Tech.* 129(1), 227 (1982)]. Temperatures above about 300° C. are therefore commonly employed for activation.

In the case of the preferred activator, copper, activation may be accomplished by, for example, solidifying a melt containing copper and silicon and comminuting the solid into particles; or by heating particles of silicon and copper together as described in U.S. Pat. No. 2,380,996; or preferably by heating mixtures of copper oxides and silicon in the presence of hydrogen and/or hydrogen chloride (see, e.g., U.S. Pat. Nos. 4,314,908 and 2,380,997); or by heating copper salts (e.g., cuprous chloride) and silicon [see, e.g., Voorhoeve, et. al., *J. Catalysis* 4, 123 (1965)]. Similar methods may be employed with activators other than copper. Various other activators and other methods of activation are known in the art and have been described in the above-mentioned monographs by Voorhoeve and Petrov, et. al.

The amount of copper required to activate the silicon is usually less than about 10% by weight of the silicon used. In general, amounts of from about 0.5% to about 3% by weight have been found to be optimum. An increase in the amount of copper catalyst within this range or even beyond has only a negligible effect on the results of the direct synthesis.

The silicon employed in the synthesis is preferably technical grade material containing about 90–98% by weight Si, with the remainder composed of such elements as Fe, Ca, Mg, Al, Sn, B, Cu, Cr, Zn, Ti, Cd, Bi and Sb and other impurities. Impurities present in technical grade silicon have been described by Lobusevich, et. al. [(*Russ. J. Appl. Chem.* 49 (10), 2236 (1976)]. Preformed metal silicides such as those of iron, calcium, magnesium and copper may also be employed in the synthesis either as individual phases or admixed with elemental silicon.

A broad range of particle sizes, e.g., 28×D mesh (i.e., no more than 500 microns) may be used in the synthesis. However, it is preferred that the copper-activated silicon particles be smaller than about 48 mesh (i.e., less than 300 microns). Smaller particle sizes contribute to good fluidization of the bed and assist heat transfer. The particle size range employed in any given reaction depends on the size of the reactor and the scale of the synthesis. In laboratory experiments, the preferred particle size range was 65×150 mesh (i.e., 104–208 microns) but this size distribution is not absolutely necessary for the success of the synthesis.

Additives known to have a demonstrably beneficial effect on the rate and selectivity of the Rochow Direct Reaction may also be preferably employed. The best known of these additives are zinc powder, anhydrous $ZnCl_2$, ZnO and $ZnCO_3$. However, others such as cadmium salts (see, e.g., U.S. Pat. No. 3,446,829), cobalt salts, antimony and bismuth salts (see, e.g., the Noll and Voorhoeve monographs, supra) are also suitable. These additives may be introduced at the silicon activation stage and/or during the reaction of tne hydrocarbon halide and hydrocarbon ether with the activated silicon particles. It is known in the art that these additives promote the formation of dialkylsilyl compounds. Consequently, their employment is expected to favor a high content of the desired organosiloxanes.

The amount of the zinc additive employed may be about 0.2–0.5% by weiqht of the silicon charged to the reactor. Larger amounts lead to increased $ZnCl_2$ formation in the reacting mass and difficult fluidization of the bed. Additionally, excess $ZnCl_2$ may be transported from the bed and enter the reaction product where it may catalyze condensation reactions of the alkoxysilanes and lead to the formation of silicone gum. While the latter are desirable products in some cases, in the present invention it is preferable to avoid their formation and obtain fluid siloxanes.

The hydrocarbon ethers which may be employed in the present invention are those having at least one, and preferably two, aliphatic hydrocarbon groups bonded to the ether oxygen, and may be represented by the general formula $R_1-O-R_2$, wherein $R_1$ and $R_2$, which may be the same or different, each represents an aliphatic hydrocarbon radical, which may be saturated or unsaturated, or an aromatic hydrocarbon radical with the proviso that at least one of $R_1$ and $R_2$ is an aliphatic hydrocarbon radical such as an alkyl radical. Thus diaryl ethers are excluded, but dialkyl ethers are suitable. Also suitable are alkyl-aryl ethers such as methylphenyl ether, ethylphenyl ether and the like. Preferred ethers are the structurally symmetric ones of the general formulae ROR, wherein R is a monovalent aliphatic hydrocarbon radical, which may be saturated or unsaturated, containing 1 to 6 carbon atoms. Representative of this class are methyl, ethyl, n-propyl, isopropyl, n-butyl, isobutyl, vinyl and allyl radicals. Structurally unsymmetric ethers such as methylethyl ether lead to siloxanes containing more than one type of alkyl residue bonded to silicon. Notwithstanding their usefulness, these mixtures are commercially less desirable than those siloxane products containing only one kind of alkyl group bonded to silicon and thus are not as preferred for purposes of the present invention. The commercial utility of the dimethylsiloxanes, and the ready availability at an inexpensive price and ease of handling in gas-solid reactions of dimethyl ether all contribute to making dimethyl ether the preferred hydrocarbon ether of this invention.

The hydrocarbon halide which may be employed in the present invention may be chosen from among those known to react with copper-activated silicon in the Rochow Direct Synthesis, and may be represented by the general formula $R_3X$, wherein $R_3$ represents a saturated or unsaturated aliphatic or aromatic hydrocarbon radical, such as an alkyl, vinyl or phenyl radical, and X represents a halogen atom. Suitable examples are methyl chloride, methyl bromide, ethyl chloride, ethyl bromide, vinyl chloride, chlorobenzene and bromobenzene. Methyl chloride and methyl bromide are the preferred hydrocarbon halides.

For the direct synthesis of cyclic and oligomeric dimethylsiloxanes devoid of halogen atoms or alkoxy groups bonded to silicon, methyl bromide is preferably employed. Methyl chloride favors formation of the precursors, dimethylmethoxychlorosilane, dimethyldimethoxysilane, dimethyldichlorosilane, $\alpha,\omega$-dichloro (dimethylsiloxanes) and $\alpha,\omega$-chloromethoxy (dimethylsiloxanes).

The total amount of gaseous reactant (i.e. hydrocarbon ether plus hydrocarbon halide) employed in this invention must be, as a minimum, sufficient to fluidize the activated silicon particles and must, of course, be less than that flow which completely discharges or elutriates the activated silicon particles from the bed before they are reacted. The minimum flow for fluidization is computed from a knowledge of the gas densities, the density and particle size distribution of the activated silicon particles and the temperature of the reaction, as described for example in the monograph, *Fluidization Engineering* by D. Kunii and O. Levenspiel, John Wiley & Sons, New York (1969). It is possible to operate the bed at many times this minimum flow and still keep the reacting activated silicon particles contained in the reactor in a fluidized state. For the laboratory preferred average particle size of about 149 microns and reaction temperatures of 300°–350° C., the minimum linear fluidization velocity is approximately 0.15 cm/sec. Operational values of 2–5 times this minimum flow are preferred.

Both the hydrocarbon halide and hydrocarbon ether must simultaneously be in contact with the activated silicon particles to realize successful direct synthesis of the desired organosiloxanes. They may be introduced to the reactor via separate conduits. However, it is preferred that metered quantities of hydrocarbon halide and hydrocarbon ether be admixed and then injected into the reactor through a common conduit. Example 3 shows that dimethyl ether and activated silicon alone do not react under the preferred conditions of this invention. Likewise, injection of dimethyl ether into the head-space of a reactor in which the Rochow Direct Synthesis was being practiced did not result in the formation of the desired dialkylsiloxanes.

At the preferred fluidization velocities, superficial contact times of about five seconds to about five minutes are obtained, and are therefore preferred, depending on the height of the fluidized bed of activated silicon particles.

The molar proportion of hydrocarbon halide to hydrocarbon ether is not critical and may be varied to determine the type of products formed during the reaction. Low hydrocarbon halide to hydrocarbon ether molar ratios (i.e., less than about 1) lead to low levels of siloxane formation and favor the formation of hydrocarbonoxy intermediate compounds such as the dialkylhaloalkoxysilanes and dialkyldialkoxysilanes. Moreover, as that ratio increases beyond about 6 to 1, formation of intermediates such as diorganodihalosilanes are favored over siloxanes. Hydrocarbon halide: hydrocarbon ether molar ratios of about 1:1 to 6:1 favor the formation of the desired cyclic and oligomeric organosiloxanes. Preferred hydrocarbon halide to hydrocarbon ether molar ratios are in the range of about 1–2.0.

When the starting reactants in the process of the instant invention are the preferred alkyl halide and dialkyl ether, all alkyl radicals being the same, the reaction product may contain the following classes of products:

1. Monomeric alkylhalosilanes of the general formula $R_aSiH_bX_{4-a-b}$, wherein a and b are integers greater than or equal to zero, (4-a-b) is greater than zero, R represents an alkyl group, and X represents a halogen atom; e.g., $(CH_3)_2SiHCl$, $(CH_3)_3SiHCl$, $CH_3SiHCl_2$, $(CH_3)_2SiCl_2$.

2. Monomeric alkylalkoxy- and alkylhaloalkoxy silanes of the general formulae $R_2Si(OR)X$ and $R_2Si(OR)_2$, wherein R and X have the same meaning; e.g., $(CH_3)_2Si(OCH_3)Cl$, $(CH_3)_2Si(OCH_3)_2$.

3. Alkylhalodisiloxanes of the general formula $R_aSi_2OX_b$, wherein R represents an alkyl group, a and b are each an integer greater than zero and $a+b=6$; e.g., $(CH_3)_3SiOSi(CH_3)_2Cl$, $(CH_3)_3SiOSiCl_2CH_3$.

4. Alkylhaloalkoxydisiloxanes of the general formula $R_aSi_2O(OR)_bX_c$, wherein R represents an alkyl group, a, b and c are each an integer greater than zero and $a+b+c=6$; e.g.,

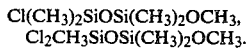
$Cl(CH_3)_2SiOSi(CH_3)_2OCH_3$,
$Cl_2CH_3SiOSi(CH_3)_2OCH_3$.

5. Hexa(alkyl)disiloxanes of the general formula $R_3SiOSiR_3$ wherein R represents an alkyl group; e.g., $(CH_3)_3SiOSi(CH_3)_3$.

6. (a) Linear trialkylsilyl-endblocked trisiloxanes and oligomeric siloxanes of the general formula $MD_nM$ wherein n is an integer of 1 to 7, $M=R_3SiO_{\frac{1}{2}}$, $D=R_2SiO$ and R is an alkyl group; e.g., $(CH_3)_3SiO[(CH_3)_2SiO]_nSi(CH_3)_3$;

6. (b) Functionalized siloxanes of the class just defined in 6(a) of the formulae $MD_nSiX_aR_b$ wherein a and b are each an integer greater than or equal to zero, $a+b=3$, and M, n, x and D are as defined above, e.g., $(CH_3)_3SiO[(CH_3)_2SiO]_nSiCl_2CH_3$; or $MD_nSi(OR)_aR_b$ wherein M, n, D, R, a and b have the same meaning; e.g.,

$(CH_3)_3SiO[(CH_3)_2SiO]_nSi(OCH_3)(CH_3)_2$.

7. Monocyclic dialkylsiloxanes of the general formula $D_n$ wherein D has the same meaning as above and n represents an integer of 3 to 8; e.g., $[(CH_3)_2SiO]_n$.

It is preferred that the process of the present invention be performed to obtain predominantly the members of Classes 6 and 7 above. The compounds of Classes 1–5 are considered to be the precursors of the desired siloxanes produced by the process of the present invention. When the preferred hydrocarbon halide, methylbromide, is employed, the members of Classes 6(a) and 7 tend to predominate; when the preferred hydrocarbon halide, methylchloride, is employed, the members of Class 6(b) tend to predominate. Generally, when the preferred operating conditions are followed, the members of Classes 6 and 7 predominate over the compounds of Classes 1–5.

Distillation of the product mixture to obtain individual compounds is not critical to the utility of this invention. The gaseous portion of the reaction product is essentially a mixture of hydrocarbon ethers and hydrocarbon halides of different composition from that at the inlet. In the preferred practice of this invention, this mixture is analyzed (e.g., by gas chromatography) to determine the hydrocarbon halide to hydrocarbon ether molar ratio, is reconstituted with additional hydrocarbon halide and/or hydrocarbon ether to obtain molar ratios in the range 1.0–2.0, and is then recycled to the direct synthesis of the siloxanes. For the higher-boiling liquid components, their normal boiling points are such that they fall into groups roughly equivalent to the classes 1 through 7 defined above. Accordingly, a distillation can be performed if desired to obtain individual distillates corresponding to each class of product.

The minimum temperature of the direct process of this invention is set by the minimum temperature at which the hydrocarbon halide reacts with the activated silicon. These temperatures are recorded in the above-cited monographs by Voorhoeve and Petrov, et. al. For example, they are 290° C. for $CH_3Cl$ and 195° C. for $C_2H_5Cl$ and for $CH_3Br$. Maximum temperatures are determined by the temperatures of onset of hydrocarbon halide pyrolysis. Optimum temperatures are those which permit both facile reaction and volatilization of the products without the complexities of pyrolysis. Accordingly, the operational temperature range for this invention at atmospheric pressure is about 250°–400° C., preferably about 325°–360° C.

The process of the present invention may be conducted at atmospheric pressure or at super-atmospheric pressures up to about 60 pounds per square inch gauge, as is conventional for the direct reaction. At higher pressures, temperatures lower than about 300°–400° C. may be employed, as is apparent to those of ordinary skill in the art. The particular pressure at which the process is operated is not critical, and those skilled in the art can select an appropriate pressure.

Of course it is to be understood that storage containers, reactors, transport lines, pumps, valves and other fittings employed in the apparatus to effect the reactions of the instant invention, all of which are conventional, and which come into contact with, or are reasonably expected to come into contact with the hydrocarbon halides, hydrocarbonhalosilanes, hydrocarbonhalohydrocarbonoxysilanes and the various siloxanes of this invention as defined above must be corrosion resistant, especially at the preferred temperatures.

The following examples, together with comparison Example 3, illustrate the preferred embodiments of the instant invention under laboratory conditions. They are not intended to limit the scope of the invention; rather, they are presented merely to facilitate the practice of the invention by those of ordinary skill in the art. The examples are based on work which was actually performed.

All experiments were conducted in laboratory Vycor fluidized bed reactor of overall length 66 cm. The upper 10 cm of the reactor was an expanded head, 6.5 cm internal diameter, while the lower 56 cm had an internal diameter of 3.3 cm. The bed height when fluidized was 25 cm, thus giving a length/diameter, L/D, ratio of 7.6. An air-driven vibrator was sometimes used to assist fluidization. A sintered glass frit at the bottom of the reactor supported the activated silicon particles end dispersed the gases as they entered the bed. Heating wire and fiberglass insulation were wrapped along the entire length of the reactor. Two Pyrex thermowells were placed vertically through the top of the reactor into the bed of activated silicon particies. One thermocouple provided feedback to the heater/controller device, the other was attached to a digital thermometer. A reservoir, vented with nitrogen, was attached to the reactor near its base just above the glass frit to permit the intermittent addition of zinc promoters and/or additional activated silicon to the bed. The junction of the reservoir and the reactor was normally kept closed by a valve. The reactor was connected to a condensing chamber by a side-arm attached to the top of the expanded head section of the reactor. The condensing chamber was maintained at $-63°$ C. to $-78°$ C. with solid carbon dioxide and isopropanol. Condensed samples of the reaction product were withdrawn, usually hourly, into weighed, chilled flasks. Unreacted methylhalide and dimethyl ether were distilled off at 23°–30° C. and the residue analyzed by gas chromatography and gas-chromatography/mass spectrometry.

The reagent gases were conveyed from their commercial cylinders to the reactor through stainless steel tubing. All gases were passed through packed beds of anhydrous calcium sulfate (obtained from W. A. Hammond and Co. under its trademark Drierite) prior to entry into the reactor in order to remove traces of moisture. Of course, all flowmeters were calibrated with the appropriate gas volumetrically with a wet-test meter and/or gravimetrically by condensing and weighing metered quantities of liquified gas.

For the experiments wherein methanol was added to the activated silicon particles along with dimethyl ether, weighed amounts of methanol were delivered by syringe pump to a heated (70°–100° C.) section of the common inlet to the reactor and therein it was vaporized and mixed with the dimethyl ether before entering the bed of activated silicon particles.

Example 1—Preparation Of Activated Silicon Particles

The reactor described above was charged with 200 gm of $65 \times 150$ mesh technical grade silicon (98.4% Si, 0.35% Al, 0.55% Fe) and 5.0 gm of cement copper (Cu°=22%, $Cu_2O$=50.4%, CuO=18.8%) and heated to 300° C. with dry nitrogen as the fluidizing gas. Thereafter, nitrogen was discontinued and HCl at 1.0 std. lit/min (i.e., measured at 21° C., 1 atm) was admitted to the reactor for one hour. A 10°–20° C. exotherm occurred during that time. Simultanenously, approximately eight percent of the silicon charged was converted to chlorosilane, principally trichlorosilane which were condensed in the refrigerated chamber. Upon the termination of HCl flow, dry nitrogen was again admitted to the bed for one hour to desorb residual chlorosilanes and Si—Cl surface species from the activated silicon particles. The bed temperature was usually increased to the reaction temperature (325°–360° C.) during this desorption step. Existence of the Si—X (X=Cl, Br) surface species on silicon surfaces following treatment of silicon with CuX or HX has been established through the experiments of Zubkov, et. al., *Dokl. Akad. Nauk, SSR* 159(3), 599 (1964); 188 (3), 594 (1969) and Miyamura, et. al., *Surf. Sci.* 72, 243 (1978).

Example 2

This example illustrates that activated silicon particles prepared as described in Example 1 react with methyl chloride to give methylchlorosilanes. Powdered $ZnCO_3$ (0.5 gm) was added to the activated silicon particles while they were under nitrogen fluidization at 325° C. The $ZnCO_3$ was placed in the above-mentioned reservoir attached to the base of the reactor and injected into the latter with a pulse of dry nitrogen. Thereafter, additional $ZnCO_3$ (0.2 gm) was injected hourly in the same manner. Methyl chloride at 0.8 std. lit/min was substituted for nitrogen as the fluidizing gas and the reaction continued for 8 hours. Gas chromatographic analysis of the hourly samples showed that steady-state conditions in the bed were attained in 2–3 hours. The steady-state parameters were 89.93 wt % $(CH_3)_2SiCl_2$, 4.58 wt % $CH_3SiCl_3$, 1.06 wt % $(CH_3)_3SiCl$, 1.11 wt % $CH_3SiHCl_2$ and a total of 3.32 wt % of the methylchlorodisilanes and methylchlorosiloxanes shown below:

$(CH_3)_3Si$—$Si(CH_3)_2Cl$
$(CH_3)_3Si$—$SiCl_3$
$Cl(CH_3)_2Si$—$SiCl_3$
$(CH_3)_3Si$—$Si(CH_3)_3$
$CH_3Cl_2Si$—$SiCl_2CH_3$
$(CH_3)_2ClSi$—$SiCl_2CH_3$
$(CH_3)_2ClSi$—$Si(CH_3)_2Cl$
$(CH_3)_3SiOSiCl_2CH_3$
$(CH_3)_2ClSiOSiCl_3$

Example 3 (For Comparison)

Together, the three experiments in this example show that dimethyl ether does not react with activated silicon particles by itself, but needs the simultaneous presence of an organohalide to do so.

(a) Silicon particles, activated with cement copper and HCl as described in Example 1, were promoted with $ZnCO_3$ as described in Example 2 and treated with 0.8 std. lit/min of dimethyl ether for 6 hrs at 325° C. No silicon-containing products were obtained. In fact, the hourly sample flasks contained only small amounts of elutriated silicon particles following the evaporation of the dimethyl ether.

(b) When, instead of desorption with $N_2$ at 325° C. for 1 hr, the desorption of the Si—Cl surface species was conducted at 265° C. for 30 mins., so as to retain more of the said Si—Cl species on the silicon particles, treatment with a mixture of 90.6 gm/hr of dimethyl ether and 34.84 gm/hr of vaporized methanol at 266° C. for one hr gave a product mixture containing 3% $(CH_3)_2Si(OCH_3)_2$, 3% $CH_3Si(OCH_3)_3$, 56% $HSi(OCH_3)_3$, 23% $Si(OCH_3)_4$ and 15% methoxydisiloxane and methylmethoxydisiloxanes. It is well known that $HSi(OCH_3)_3$, and $Si(OCH_3)_4$ are the principal products of the direct synthesis of methanol with activated silicon particles (see, e.g., U.S. Pat. Nos. 3,072,700 and 2,473,260). Their formation persisted throughout the duration of the experiment. However, synthesis of the methylmethoxysilanes was not sustained beyond the first hour.

(c) Reaction of the freshly activated and only partially desorbed silicon particles [Example 2(b)] with 89.7 gm/hr of vaporized methanol for 5 hrs followed by 6 hrs with a mixture of 90.6 gm/hr of dimethyl ether and 92.9 gm/hr. of vaporized methanol did not result in methylmethoxy silane formation. All eleven hourly samples showed $HSi(OCH_3)_3$, $Si(OCH_3)_4$, and methoxydisiloxanes as the only products.

Without being bound by theory, these results may be explained as follows: Surface Si—Cl moieties reacted with dimethyl ether (equation 10) to produce methyl chloride:

$$Si-Cl + (CH_3)_2O \rightarrow Si-OCH_3 + CH_3Cl \quad (10)$$

The latter reacted with the activated silicon particles to produce $(CH_3)_2SiCl_2$ and $CH_3SiCl_3$ as well as additional Si—Cl surface species. The methylmethoxysilanes arose via equations 11–14:

$$(CH_3)_2SiCl_2 + 2CH_3OH \rightarrow (CH_3)_2Si(OCH_3)_2 + 2HCl \quad (11)$$

$$(CH_3)_2SiCl_2 + 2(CH_3)_2O \rightarrow (CH_3)_2Si(OCH_3)_2 + 2CH_3Cl \quad (12)$$

$$CH_3SiCl_3 + 3CH_3OH \rightarrow CH_3Si(OCH_3)_3 + 3HCl \quad (13)$$

$$CH_3SiCl_3 + 3(CH_3)_2O \rightarrow CH_3Si(OCH_3)_3 + 3CH_3Cl \quad (14)$$

Eventually, their formation was terminated due to the loss of $CH_3Cl$ from the bed. It is to replenish the Si—Cl surface groups that $CH_3Cl$ is required in this direct synthesis.

Example 4

This example shows that the direct synthesis of siloxanes ensues from the use of $(CH_3)_2O$ and $CH_3Cl$ mixtures.

The reaction was performed as described in Example 2 except that the feed gas contained 0.37 std. lit/min. $(CH_3)_2O$ plus 0.54 std. lit/min $CH_3Cl$. The volumetric ratio, $CH_3Cl/(CH_3)_2O$, was 1.46 and the molar ratio, 1.44. Two cumulative, three-hour samples were collected. Gas-chromatographic/mass spectrometric analysis of each sample following distillation of the excess $(CH_3)_2O$ and $CH_3Cl$ revealed:

$(CH_3)_2SiHCl$
$(CH_3)_3SiCl$
$(CH_3)_2SiCl_2$
$(CH_3)_2Si(OCH_3)Cl$
$(CH_3)_3SiOSi(CH_3)_2Cl$
$[(CH_3)_2SiO]_4$
$Cl(CH_3)_2SiOSi(CH_3)_2OCH_3$
$(CH_3)_3SiOSiCl_2CH_3$
$Cl_2CH_3SiOSi(CH_3)_2OCH_3$
$(CH_3)_3SiOSi(CH_3)_2OSiCl_2CH_3$
$(CH_3)_3Si[OSi(CH_3)_2]_2OSiCl_2CH_3$

Note that compared with Example 2, no disilanes were detected and that many more siloxanes were formed. Total content of linear, cyclic and functionalized siloxanes was 8.09 wt %. The direct synthesis of methylsiloxanes from dimethyl ether and methyl chloride was accomplished in a fluidized bed at atmospheric pressure.

Example 5

This Example shows that $CH_3Br$ and $(CH_3)_2O$ react with activated silicon to yield a higher content of siloxanes than was realized with $CH_3Cl$ and $(CH_3)_2O$ under analogous reaction conditions.

(a) The reaction of Example 2 was repeated with 0.83 std. lit./min $CH_3Br$ over a 22 hour period. 591.34 gm of mixed methylbromosilanes was obtained after distillation of excess methylbromide. The product contained 41.10 wt % $(CH_3)_2SiBr_2$, 33.06 wt % $CH_3SiBr_3$, 22.23 wt % $(CH_3)_3SiBr$, 0.57 wt % $(CH_3)_2SiHBr$, 0.22 wt % $CH_3SiHBr_2$ and 2.92 wt % methylbromodisilanes.

(b) Following the above reaction with methyl bromide, the feed gas was changed to 0.373 std. lit./min. $(CH_3)_2O$ and 0.55 std. lit/min. $CH_3Br$. The volumetric ratio, $CH_3Br/(CH_3)_2O$ was 1.48 and the molar ratio 1.49. Reaction was continued for 7 hrs at 325° C. The product left after evaporation of excess $(CH_3)_2O$ and $CH_3Br$ was a viscous, pleasant-smelling liquid, which did not fume in contact with moisture as did the mixed methylbromosilanes. Gas-chromatographic/mass-spectrometric analysis revealed the presence of the following methylmethoxy silanes and linear and cyclic methylsiloxanes:

$(CH_3)_3SiOCH_3$
$(CH_3)_3SiOSi(CH_3)_3$
$(CH_3)_2Si(OCH_3)_2$
$(CH_3)_3Si[OSi(CH_3)_2]_nOCH_3$ n = 1, 2, 3 and 4
$(CH_3)_3Si[OSi(CH_3)_2]_nOSi(CH_3)_3$ n = 1, 2, 3 and 4
$[(CH_3)_2SiO]_n$ n = 3, 4, 5, 6 and 7

The total content of siloxanes in the product was 83.58 wt %. Less than 1% of $(CH_3)_2Si(OCH_3)_2$ was formed.

What is claimed is:

1. A process for preparing cyclic and oligomeric organosiloxanes comprising reacting a hydrocarbon ether and a hydrocarbon halide with a fluidized or agitated bed of activated silicon particles at a maximum contact time of 5 minutes, and continuously withdrawing products from said reaction.

2. The process of claim 1 wherein said reaction is conducted at a temperature greater than the boiling points of the reactants and products.

3. The process of claim 2 wherein said temperature is about 250°–400° C.

4. The process of claim 2 wherein said temperature is about 325°–360° C.

5. The process of claim 3 or 4 wherein said reaction is conducted at atmospheric pressure.

6. The process of claim 1 wherein said reaction is conducted at a superatmospheric pressure up to about 60 pounds per square inch.

7. The process of claim 1 wherein said silicon particles are activated with a member selected from the group consisting of copper and silver.

8. The process of claim 1 wherein said silicon particles are activated with copper.

9. The process of claim 8 wherein said copper-activated silicon particles are prepared by heating mixtures of copper oxides and silicon metal in the presence of hydrogen chloride.

10. The process of claim 9 wherein the activation reaction is conducted at a temperature above about 300° C.

11. The process of claim 8 wherein the amount of copper in said activated silicon particles is less than about 10% by weight, based on the weight of silicon.

12. The process of claim 8 wherein the amount of copper in said activated silicon particles is from about 0.5 to about 3% by weight, based on the weight of silicon.

13. The process of claim 1 wherein the particle size of said activated silicon particles is smaller than 300 microns.

14. The process of claim 1 wherein said reaction is conducted in the presence of an additive selected from the group consisting of zinc powder, anhydrous $ZnCl_2$, ZnO and $ZnCO_3$.

15. The process of claim 9 wherein said heating step is conducted in the presence of an additive selected from the group consisting of zinc powder, anhydrous $ZnCl_2$, $ZnO$ and $ZnCO_3$.

16. The process of claim 1 wherein said organosiloxanes are dimethylsiloxanes.

17. The process of claim 1 wherein said hydrocarbon ether is a compound represented by the formula $$R_1-O-R_2$$

wherein $R_1$ and $R_2$, which may be the same or different, each represent a saturated or unsaturated aliphatic hydrocarbon radical or an aromatic hydrocarbon radical, with the proviso that at least one of $R_1$ and $R_2$ is an aliphatic hydrocarbon radical.

18. The process of claim 17 wherein $R_1$ and $R_2$ are the same monovalent aliphatic hydrocarbon radical having from 1 to 6 carbon atoms.

19. The process of claim 1 wherein said hydrocarbon ether is dimethyl ether.

20. The process of claim 1 wherein said hydrocarbon halide is a compound represented by the formula $R_3X$ wherein $R_3$ represents a saturated or unsaturated aliphatic hydrocarbon radical or an aromatic hydrocarbon radical, and X represents a halogen atom.

21. The process of claim 20 wherein $R_3$ is selected from the group consisting of alkyl, vinyl and phenyl radicals.

22. The process of claim 1 wherein said hydrocarbon halide is methyl chloride.

23. The process of claim 1 wherein said hydrocarbon halide is methyl bromide.

24. The process of claim 1 wherein gaseous hydrocarbon ether and hydrocarbon halide are fed to the reaction in an amount sufficient to fluidize the activated silicon particles.

25. The process of claim 24 wherein said amount is at least that amount necessary to provide a linear fluidization velocity of about 0.15 cm/sec.

26. The process of claim 1 wherein said hydrocarbon halide and said hydrocarbon ether are mixed and then the resulting mixture is fed to said reaction.

27. The process of claim 1 wherein the reaction contact time is from about 5 seconds to about 5 minutes.

28. The process of claim 1 wherein the molar proportion of hydrocarbon halide:hydrocarbon ether is from about 1:1 to about 6:1.

29. The process of claim 1 wherein the molar proportion of hydrocarbon halide:hydrocarbon ether is from about 1:1 to 2:1.

30. The process of claim 1 further comprising recycling the gas reaction product to the reaction.

31. The process of claim 30 wherein the molar ratio of hydrocarbon halide:hydrocarbon ether fed to the reaction is from about 1:1 to about 2:1, and wherein said gas reaction product is reconstituted with additional hydrocarbon halide and hydrocarbon ether to obtain a gas mixture having said molar ratio and thereafter is recycled to said reaction.

32. A process for preparing cyclic and oligomeric dimethylsiloxanes comprising reacting dimethyl ether and a hydrocarbon halide selected from the group consisting of methyl chloride and methyl bromide with a fluidized bed of activated silicon particles at a contact time of about 5 seconds to about 5 minutes, and continuously withdrawing product from said reaction.

33. The process of claim 32 wherein said silicon particles are activated with copper.

34. The process of claim 33 wherein said copper-activated silicon particles are prepared by heating mixtures of copper oxides and silicon metal in the presence of hydrogen chloride.

35. The process of claim 32 wherein said hydrocarbon halide is methyl chloride.

36. The process of claim 32 wherein said hydrocarbon halide is methyl bromide.

* * * * *